United States Patent [19]
Saadat et al.

[11] Patent Number: 5,496,309
[45] Date of Patent: Mar. 5, 1996

[54] CATHETER DEVICE UTILIZING A LASER BEAM LATERALLY DIRECTED BY A HIGH INDEX PRISM IN A LIQUID MEDIUM

[75] Inventors: Vahid Saadat, Irvine; Marvin P. Loeb, Huntington Beach; L. Dean Crawford, Irvine, all of Calif.

[73] Assignee: Trimedyne, Inc., Irvine, Calif.

[21] Appl. No.: 239,338

[22] Filed: May 6, 1994

[51] Int. Cl.⁶ ........................................... A61B 17/36
[52] U.S. Cl. ........................... 606/15; 606/7; 606/17
[58] Field of Search ................... 606/2, 3, 7, 14, 606/15, 16, 17, 23, 13, 1; 607/88, 89

[56] References Cited

U.S. PATENT DOCUMENTS

| | | | |
|---|---|---|---|
| 4,349,032 | 9/1982 | Koyata | 128/4 |
| 4,592,353 | 6/1986 | Daikuzono | 606/17 X |
| 4,740,047 | 4/1988 | Abe et al. | 128/4 X |
| 4,832,024 | 5/1989 | Boussignac et al. | 606/15 X |
| 5,041,121 | 8/1991 | Wondrazek et al. | 606/15 X |
| 5,146,917 | 9/1992 | Wagnières et al. | 606/17 X |
| 5,151,096 | 9/1992 | Khoury | 606/17 X |
| 5,163,935 | 11/1992 | Black et al. | 606/17 |
| 5,190,536 | 3/1993 | Wood et al. | 606/17 X |
| 5,209,748 | 5/1993 | Daikuzono | 606/17 X |
| 5,242,438 | 9/1993 | Saadatmanesh et al. | 606/17 |
| 5,246,436 | 9/1993 | Rowe | 606/17 X |

FOREIGN PATENT DOCUMENTS

| | | | |
|---|---|---|---|
| 778276 | 7/1957 | United Kingdom | 128/4 |

*Primary Examiner*—Stephen C. Pellegrino
*Assistant Examiner*—Michael Peffley
*Attorney, Agent, or Firm*—Olson & Hierl, Ltd.

[57] ABSTRACT

A laser energy delivery catheter emits energy laterally relative to the longitudinal axis of the catheter. The catheter distal end is a cylindrical housing provided with a sidewall aperture. Within the housing is mounted a prism spaced from the distal end of a fiber optic. The refractive index of the prism is higher than the refractive indices of the fiber optic and the coupling liquid medium. A liquid medium is utilized to cool the device when in use, and may also be utilized to optically couple the fiber optic and the prism. The catheter can be configured as a rigid or semi-rigid, hand held surgical instrument, or as a flexible device that can be inserted into body lumens through an endoscope.

18 Claims, 4 Drawing Sheets

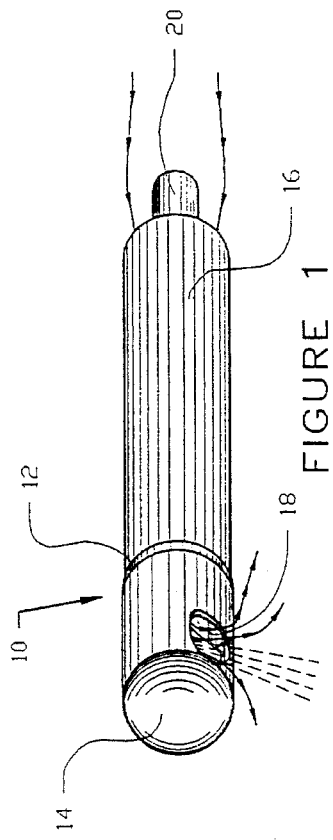
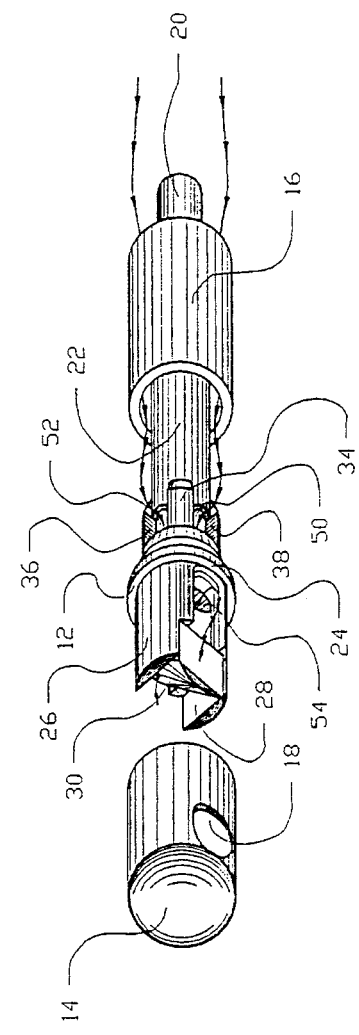
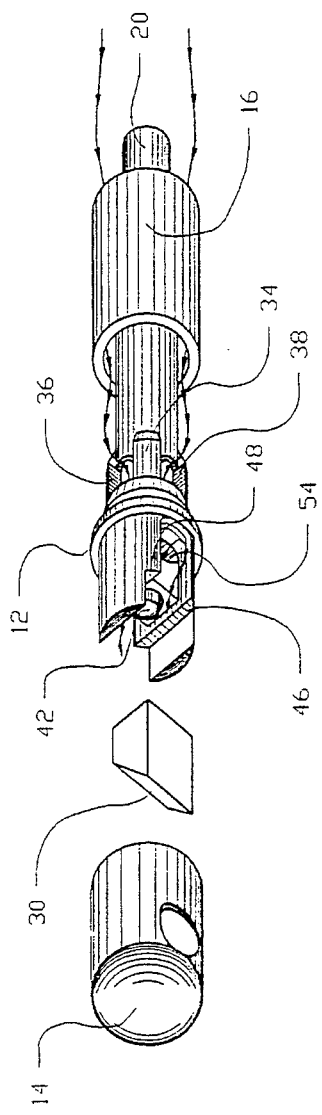

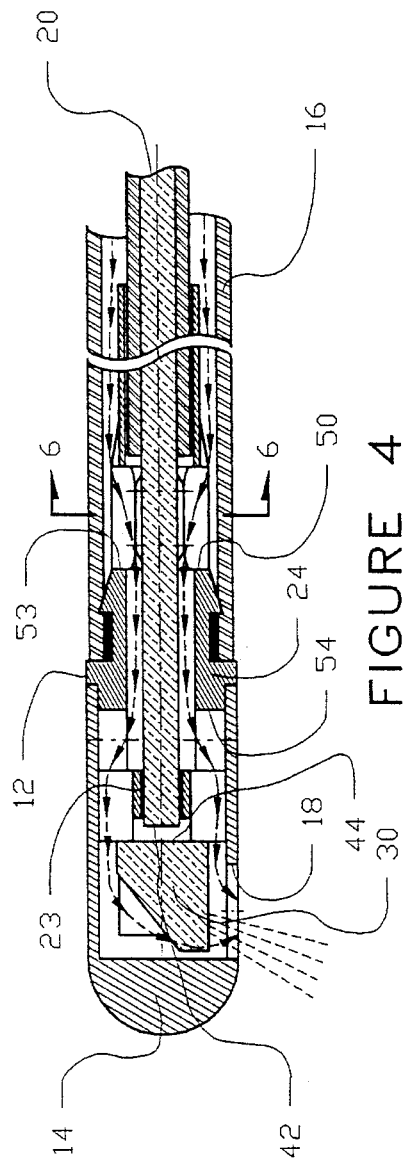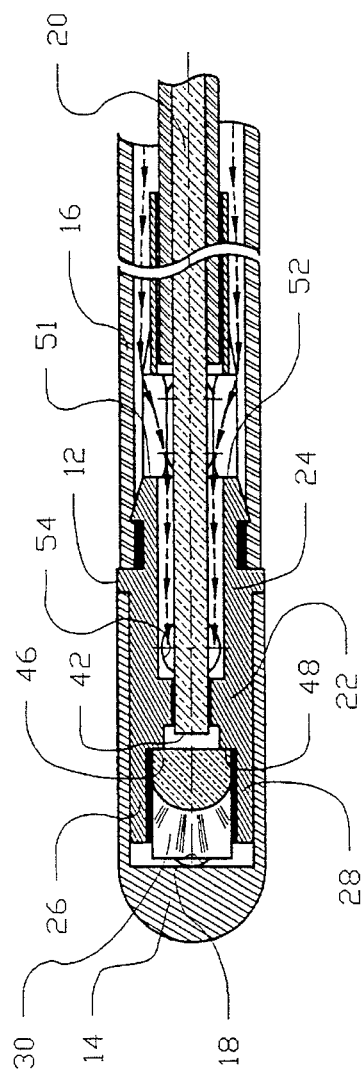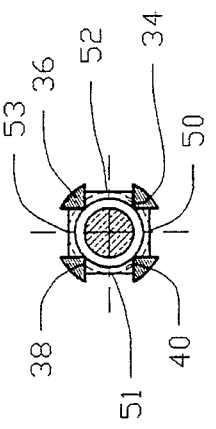

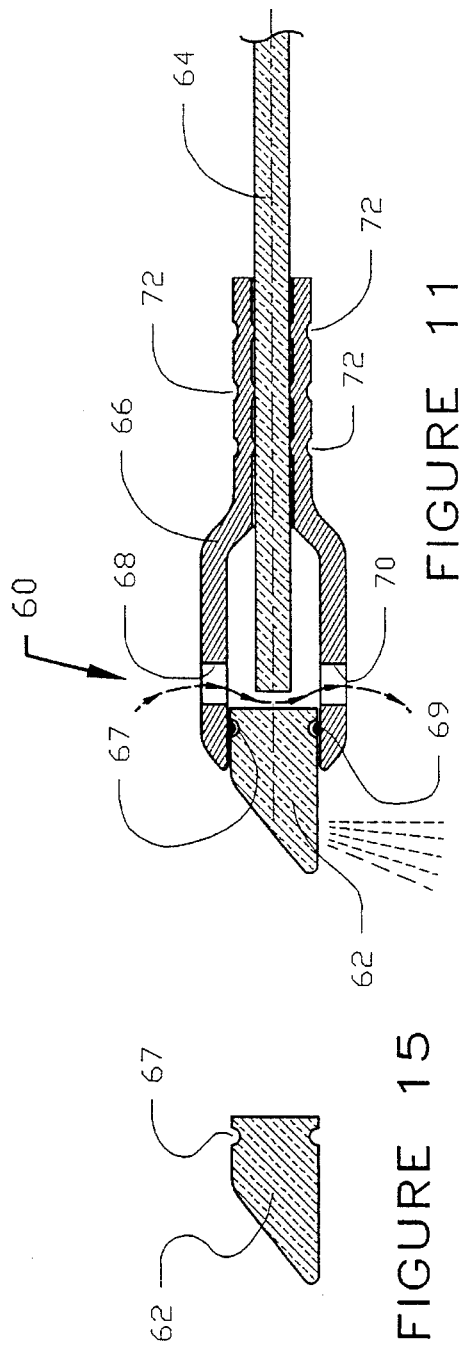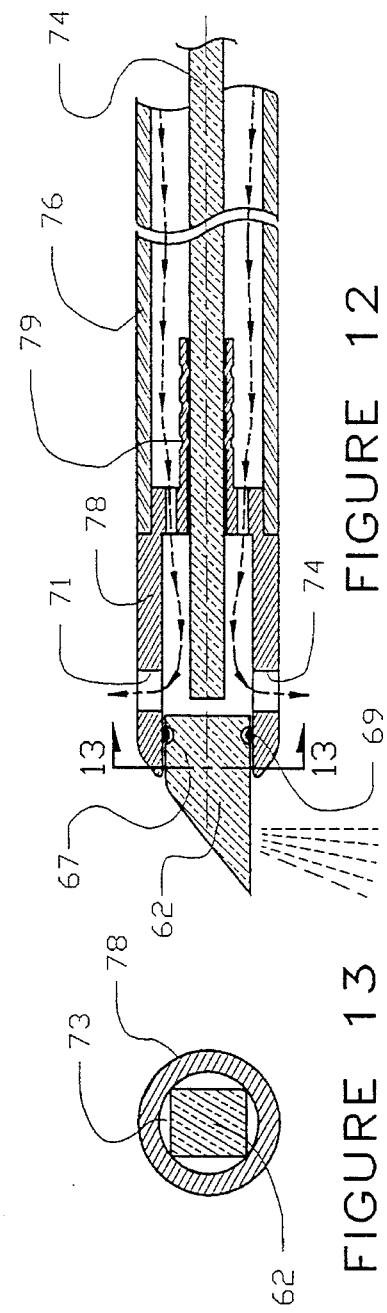

CATHETER DEVICE UTILIZING A LASER BEAM LATERALLY DIRECTED BY A HIGH INDEX PRISM IN A LIQUID MEDIUM

BACKGROUND OF THE INVENTION

1. Field of the Invention

The present invention relates to medical devices that transmit laser energy. Specifically, the present invention relates to fiber optic laser energy delivery devices that emit a laser beam substantially laterally relative to the longitudinal axis of the fiber optic in a liquid medium.

2. Description of the Prior Art

In conventional laser energy delivery devices, a laser beam is emitted from the distal end of one or more optical fibers toward the point of application in the human body. Medical applications of lasers, such as in urology, gynecology, general surgery, orthopedics, ophthalmology and other surgical procedures, sometimes require laser energy to be emitted laterally from the axis of the optical fiber, so that, in urological applications for example, the lateral lobes of the prostate may undergo ablation and/or coagulation to create an enlarged region or passage for an enhanced fluid flow.

A prism can be used to laterally reflect light energy, so long as the index of refraction of the medium surrounding the reflective surface of the prism is substantially lower than the index of refraction of the prism itself, provided the reflective surface of the prism is at or below the critical angle for total internal reflection. This critical angle depends on the ratio of the respective refractive indices between the material of the prism and that of the environment or adjoining substance immediately outside the prism's reflective surface (i.e., the boundary interface). In order to achieve total internal reflection, for a given lateral reflection angle, a substance such as air (with a refractive index of about 1) can be used to assure a sufficiently low refractive index relative to that of a glass prism (refractive index 1.46). As a result, glass prisms function properly in an air environment. However, in water (refractive index 1.33) or in saline (refractive index about 1.33, depending on concentration), glass prisms do not effectively reflect light energy laterally substantially close to 90 degrees because the difference in refractive indices between the glass and the ambient medium is not great enough.

Moreover, surrounding the prism with air has disadvantages. One such disadvantage is that an enclosure transparent to the wavelength of energy being used, such as a glass encapsulating sleeve, is needed to contain and maintain an air environment at the prism interface. This, in turn, requires that the prism be positioned in precise orientation within the sleeve. To achieve this, a very tedious alignment procedure, difficult to accurately replicate in production, is involved. On the other hand, if the prism is not in precise alignment, internal reflection may not be achieved, or a laser beam in an errant direction may be emitted. Affixation of the glass encapsulating sleeve to the buffer coating or cladding of an optical fiber in an airtight manner is also difficult to assure in production.

Another problem with a glass sleeve is that an output power loss of five to ten percent may be experienced due to scattering and back reflection from the sleeve. This is a significant and undesirable power loss.

In surgical devices that come in contact with tissue it is also difficult to maintain the glass encapsulating sleeve at a sufficiently low temperature to prevent tissue from sticking thereto. If this happens, the temperature of the sleeve can quickly rise to the point of destruction, with the potential for leaving fragments of the glass sleeve in the body, which might necessitate surgery to remove them.

Still another problem with the glass encapsulating sleeve is that it is fragile. Physical stresses exerted during insertion through endoscopes or guiding catheters, or during the lasing procedure could cause the sleeve to break, leaving glass fragments at the medical procedure site and causing complications to the patient that might require an invasive surgical procedure to correct.

While laser energy may be laterally reflected from a polished metal surface in a fluid medium, some of the laser energy may be absorbed by the metal surface, thereby raising its temperature. If the metal surface is contaminated by tissue or body oils, the temperature of the metal surface can rapidly increase, causing the metal to deteriorate or melt.

Therefore, it would be desirable to have a medical device that reflects the laser energy laterally in a fluid medium without the need for a metal reflecting surface or glass encapsulating sleeve. The present invention provides such a device.

SUMMARY OF THE INVENTION

A laser energy delivery catheter for lateral transmission of laser energy in a liquid medium is contemplated by the present invention. Laser energy is transmitted through an optical fiber to a prism with a relatively high index of refraction relative to the surrounding liquid medium. Within the prism, laser energy is reflected from a beveled reflecting surface of the prism and directed laterally. A liquid interface between the distal end of the optical fiber and the proximal end of the prism is provided to reduce laser energy coupling losses at the interface when the device is in use.

A device embodying the present invention provides increased efficiency and reliability since there is no need for a glass encapsulating sleeve. The liquid medium that surrounds the prism when the device is in use also cools the distal end of the optical fiber, the prism, and the tissue at the site of the medical procedure.

The present invention also provides for distinct advantages in manufacturability. The prism, instead of a triangular shape that is difficult to mount and orient inside a needle, cannula or housing, can be cut from a block of a material having a relatively high refractive index, such as silica doped with lead, barium, sodium, titanium, and other oxides, for example, SFL-57 from Schott Glass Technologies, Inc, Duryea, Pa., with a refractive index of 1.811 at 1060 microns, or synthetic sapphire, which has refractive index of 1.745 at 1060 microns, into an elongated, transparent rod having a rectangular cross section. The distal surface of the rod can be inclined at an angle or angles consistent with the critical angle required to provide total internal reflection of the incident radiant energy in a liquid medium laterally from the longitudinal axis of the catheter. When a transparent rod with a prism-shaped distal end is inserted into a matching recess in a housing, orientation of the prism relative to the fiber optic can be positively and easily controlled.

A catheter embodying the present invention includes an elongated, substantially cylindrical housing that defines a recess for a prism or "rod bearing prism", a confined flow passageway for a liquid medium, a sidewall aperture, a prism mounted in the housing, and a fiber optic positioned to deliver laser energy to the prism.

The distal end of the fiber optic is also mounted in the cylindrical housing, and the proximal end of the fiber optic is adapted for coupling to a laser source. The prism may abut or be spaced from the distal end of the fiber optic and is positioned to receive a laser beam emitted by the fiber optic at its distal end, and to direct the emitted beam outwardly through the sidewall aperture in the housing. The refractive index of the prism is higher than that of the fiber optic and of the liquid medium that serves to optically couple the fiber optic to the prism as well as to cool the prism while the catheter is in use. Use of a liquid between the emitting surface of the fiberoptic and the receiving surface of the prism substantially reduces the reflection losses therefrom.

BRIEF DESCRIPTION OF THE DRAWINGS

In the drawings,

FIG. 1 is a perspective view showing the distal end of a laser energy delivery catheter embodying the present invention;

FIG. 2 is a partially exploded perspective view of the device shown in FIG. 1;

FIG. 3 is a further exploded perspective view of the device shown in FIG. 1;

FIG. 4 is a side elevational view showing the device of FIG. 1 in section;

FIG. 5 is a plan view showing the device of FIG. 1 in section;

FIG. 6 is a sectional view taken along plane 6—6 in FIG. 4;

FIG. 11 illustrates another embodiment of the current invention;

FIG. 12 shows an embodiment similar to that of FIG. 11 but with the addition of forced coaxial irrigation;

FIG. 13 shows the cross sectional view taken at plane 13—13 in FIG. 12;

FIG. 14 shows another embodiment of a suitable high index prism;

FIG. 15 is a side elevational view of the prism utilized in the embodiment shown in FIG. 11; and FIG. 16 is a side elevational view of an alternate prism that can be used in practicing the present invention.

DETAILED DESCRIPTION OF PREFERRED EMBODIMENTS

Figure 8:
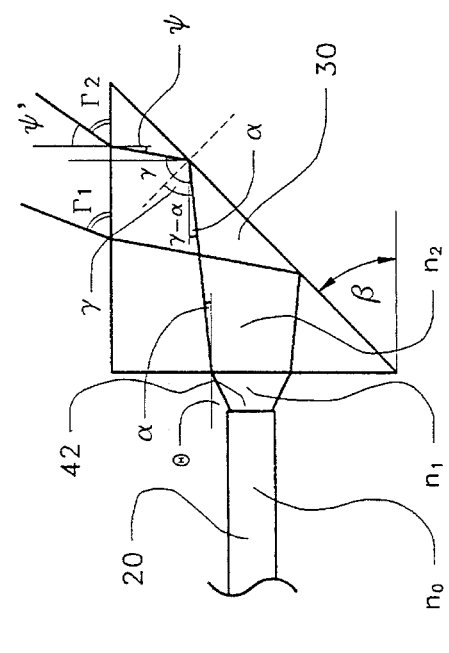
FIG. 8 illustrates a ray trace for the fiber and the high index prism.

The present laser delivery catheter can be used in a body lumen, organ, cavity or a surgically created passageway, where it is advantageous to apply laser energy laterally relative to the catheter's longitudinal axis. The present device is suitable for coagulating, cutting or ablating tissue, cartilage or other substances. Accordingly, the present device has utility in medical applications, such as urology, gynecology, general surgery, orthopedics, ophthalmology and other surgical procedures.

Referring to the drawings, FIG. 1 shows a catheter distal end 10 which is a substantially cylindrical housing constituted by frame 12 and hollow cap 14. Frame 12 is mounted to flexible tubing 16, through which optical fiber 20 extends. Hollow cap 14 is provided with sidewall aperture 18. Hollow cap 14 together with frame 12 and tubing 16 define a housing or recess for the prism and optical fiber 20, as well as a confined flow passageway for a liquid medium, such as water or saline, that may also serve as an optical coupling medium as well as a cooling medium and/or irrigation medium when the catheter embodying the present invention is in use. The flow of liquid medium (i.e., water or saline) through the catheter housing and out through sidewall aperture 18 is indicated by series of connected arrows.

Referring to FIGS. 2 and 3, frame 12 is a hollow, apertured tubular member having a cylindrical body portion 22, collar 24 that surrounds body portion 22 at one end thereof, and grips or leafs 26 and 28 that extend away from collar 24 toward the distal end of the catheter. Leafs 26 and 28 hold prism 30 therebetween, and are received within hollow cap 14. Leafs 26 and 28 as well as hollow cap 14 are in an interference fit in relationship with one another. If desired, cap 14 can be adhesively secured to leafs 26 and 28 or welded thereto.

There are four struts connecting the cylindrical body portion 22 and the collar 12. Three of these struts are shown in FIG. 2. Struts 34, 36 and 38 form a bridge between the body portion 22 and the collar 24 of frame 12. The fourth strut is not visible. In addition, these struts form four apertures, of which two are shown in FIG. 2. Apertures 50 and 52 allow the liquid medium (i.e., water or saline) to flow between the cylindrical body portion 22 and into the space defined by the two leaflets. Aperture 54 is formed between leaf 26 and 28 and collar 24. The liquid medium flows out of the two sides of the aperture 54 and across the input and reflective surfaces of the prism 30.

Fiber optic 20 extends into the cylindrical body portion 22 and is mounted thereto as will be described in greater detail hereinbelow.

As best seen in FIGS. 4, 5 and 6, the distal end of fiber optic 20 extends into the space defined, in part, by hollow cap 14 and is spaced from prism 30. The spacing between distal end face 42 of fiber optic 20 and input or incident face 44 of prism 30 is determined by shoulders 46 and 48 at the base of leafs 26 and 28, respectively. The spacing between the prism 30 and the distal end face 42 of fiber optic 20 is determined in part by the desired width of the emitted laser beam. Usually the spacing is in the range of about 5 to about 20 mils (125 µm to 510 µm), preferably about 10 mils to about 15 mils (255 µm to 350 µm).

FIG. 6 is the cross sectional view taken along plane 6—6 of FIG. 4. Apertures 50, 51, 52 and 53 are formed in between the strut pairs (34, 40) (38, 40) (34, 36) and (36, 38) respectively. The fiberoptic is centered within the aforementioned struts.

Apertures 50, 52 and 54 in frame 12 define liquid pathways for the liquid medium within cylindrical body portion 22.

Prism 30 can be synthetic sapphire (refractive index 1.745), (SFL-57; refractive index about 1.811), amorphous glass containing Ge, As and Se (AMTIR-1; refractive index 2.51), and the like.

The external dimensions of the catheter distal end, i.e., the cylindrical housing, can vary depending upon the desired end use of the catheter. For use in body lumens, the outside diameter of the cylindrical housing usually is in the range of about 0.5 to about 4 millimeters, preferably about 1 to about 2.5 millimeters. Prism 30 can have a flat or curved input face, output face and reflecting surface. If the aforementioned surfaces are flat, the ultimate divergence of the emitted beam from the prism will be determined by the divergence out of the fiberoptic and the angle of emission out of the output face. Consequently the spot size of the beam at a given distance from the emitting surface of the prism will also be determined largely by the divergence of the beam out of the fiber.

Figure 7A:
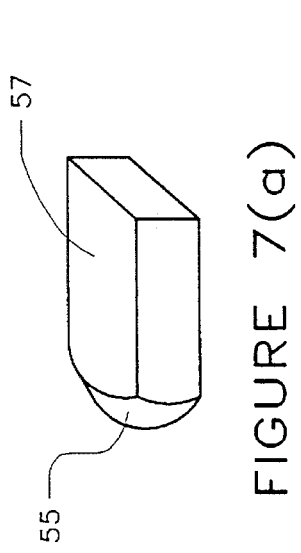
FIGS. 7(a) and 7(b) illustrate alternative prism configurations.

In one embodiment of the invention, as shown in FIG. 7(a), the totally internal reflecting (TIR) surface 55 of the prism 57 can be rounded to form a convex physical surface. This convex physical surface will act as a concave TIR surface which will increase the effective divergence of the laser beam. The plane of the arc defined by such curvature will need to be parallel to the emitting face of the prism in order to laterally reflect substantially all of the incoming light beam.

Figure 7B:
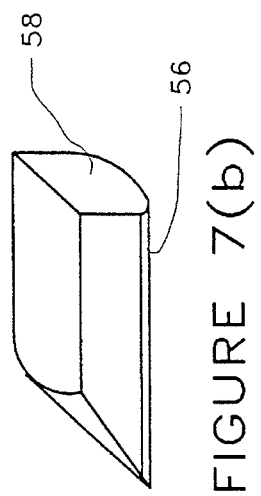

Alternatively, as shown in FIG. 7(b), the emitting surface 56 of the prism 58 can be rounded to form a convex physical surface to achieve the same diverging effect.

The aforesaid increased divergence of the beam will increase the spot size formed at a fixed distance from the tip of the catheter and reduce the energy density thereof, compared to the embodiment incorporating a prism with either a flat reflective surface or a flat emissive surface. The increased divergence may have beneficial effects by creating a substantially coagulative effect, instead of an ablative effect, due to the lower energy density.

FIG. 8 shows the propagation of light rays into and out of the high index prism. The angle at which these light rays travel within the prism is shown as $\alpha$ and can be calculated by (1)

$$\alpha = \text{Arcsin}\left(\frac{n_1 * \sin(\theta)}{n_2}\right) \quad (1)$$

where $n_1$ is the index of refraction of the surrounding medium, $n_2$ is the index of refraction of the prism and $\theta$ is the angle between the most divergent ray exiting the fiber and the normal to the input surface of the prism.

The prism is cut at angle $\beta$ with respect to the output face of the prism. Angle $\beta$ can be found by $$\beta = 90 - \theta c - \alpha \quad (2)$$

where $\theta c$ is the critical angle of the prism liquid interface and can be calculated by (3)

$$\theta c = \text{Arcsin}\left(\frac{n_1}{n_2}\right) \quad (3)$$

For example, for the case of SFL57 ($n_2$=1.811 at 1060 nm) in a water environment (n=1.33) and with a fiber of numerical aperture (NA)=0.22 ($\theta$=9.55 degrees) $\beta$ is found to be 35.75 degrees, while $\alpha$ is equal to 6.99 degrees. Fixing $\beta$ at 35.75 degrees and substituting −6.99 degrees and +6.99 degrees for $\alpha$, $\Gamma_1$ and $\Gamma_2$ are found to be 74.2 and 54.0 degrees respectively. Equation (4) is used to calculate the emission angles.

$$\Gamma = 90 \text{ Arcsin}\left(\frac{n_2 * \sin(90 - 2\beta + \alpha)}{n_1}\right) \quad (4)$$

Figure 9:
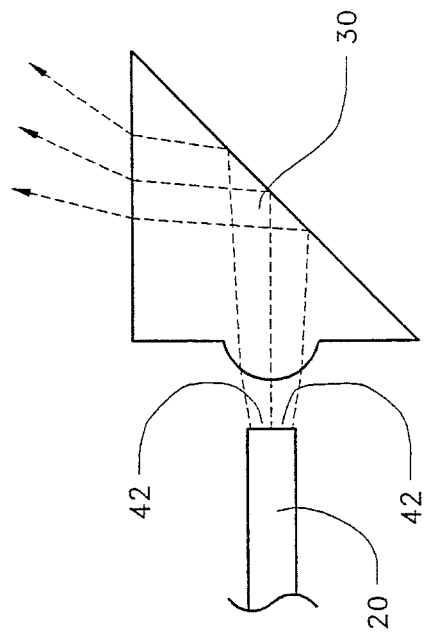
FIG. 9 illustrates a prism similar to that of FIG. 8 but with the addition of a collimating lens on the input surface.

FIG. 9 shows another embodiment of the current invention, in which a convex surface has been formed on the input end of the prism 30. The convex surface acts as a lens and serves to collimate the light energy emitted from the fiberoptic distal end 42. Consequently the angle at which such rays travel through the material would be reduced and that would allow the angle $\Gamma$ to be closer to the critical angle $\theta c$. This would result in the final angles of emission to be closer to 90 degrees.

Figure 10:
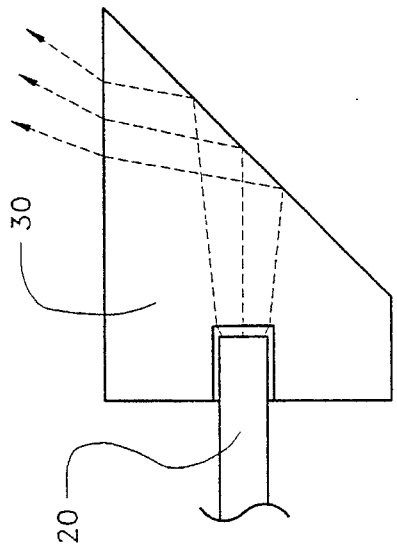
FIG. 10 illustrates a prism similar to that of FIG. 8 but with a recess in the input surface of the prism adapted to receive the distal end of a fiber optic.

If desired, as shown in FIG. 10, a recess can be provided in the incident face of the prism, and the distal end of the fiber optic may be positioned therewithin, so as to reduce scattering and attendant energy losses.

Another embodiment of the present invention is shown in FIG. 11, where catheter device 60 comprises prism 62 and fiber optic 64 mounted to housing 66, which can consist of two halves welded or glued together. Fiber optic 64 is spaced from prism 62. Housing 66 is hollow, defines a confined flow passageway for an ambient liquid medium, e.g., water or saline, and is provided with apertures 68 and 70 that permit the liquid medium to pass therethrough. The proximal end of fiber optic 64 is adapted for coupling to a laser source. Liquid medium within housing 66 provides optical coupling of fiber optic 64 to prism 62 which has a refractive index that is sufficiently higher than the refractive index of the surrounding liquid medium to permit total internal reflection of the light energy to occur. Housing 66 is secured to fiber optic 64 by crimping sleeve 72 unitary with housing 66 or, optionally, by an adhesive such as epoxy resin or the like, or both.

Prism 62 is rod-shaped and is made of a transparent material such as synthetic sapphire, which has (a) an index of refraction sufficiently high to cause laser energy transmitted thereinto to be emitted substantially laterally from the longitudinal axis thereof when surrounded by a given liquid medium and (b) a melting point sufficiently high to preclude melting or other damage thereto when in direct contact with tissue during lasing.

This embodiment can be used (a) in a non-contact mode, directing laser energy laterally in a fluid medium from prism 62 into the target tissue to coagulate the same to a chosen depth, which tissue will slough-off or be absorbed by the body over a period of several weeks, as well as, after coagulation of the tissue in the manner described in (a) above, (b) in a contact mode to vaporize or ablate tissue by placing the distal tip of prism 62 directly in contact with the tissue, thereby immediately removing a portion of the coagulated tissue constricting or obstructing a body lumen or cavity. The distal tip of the prism 62 can be rounded to minimize the risk of breakage and damage to body tissues.

In the case of benign enlargement of the prostate, deep coagulation of the prostate gland using the present device in a non-contact mode will, over a period of weeks, restore urine flow, as the coagulated tissue is sloughed-off. However, even though a small amount of tissue may be vaporized during the lasing, due to edema (swelling) of tissue as a result of the coagulation procedure, a drainage tube must be inserted and worn with a urine collection bag by the patient for a period of several days, as the patient would otherwise be unable to urinate. Following the coagulation procedure described above, the device described in this embodiment can be used in contact mode to remove a desired amount of coagulated tissue without bleeding, to offset the edema, and to enable the patient to either (a) immediately urinate without the need for a drainage tube or (b) wear a drainage tube for a substantially shorter period of time before being able to urinate normally.

Prism 62 can be made from a square or rectangular cross section rod, as well as from a cylindrical or oval rod, whose distal end has been beveled at an aforementioned angle $\beta$. To insure that prism 62 is not dislodged from housing 66 depressions 67 can be cut in the outer surfaces of prism 62, and ridges 69 of housing 66 matchingly engage therewith. Side elevation contour of prism 62 is shown in FIG. 15.

As seen in FIG. 12, flexible catheter 76 is adhesively attached to frame 78. Fiber optic 74 is secured to sleeve 79 that extends rearwardly from frame 78. Fluid flow through apertures 71, 74 in frame 78 is indicated by connected arrows.

FIG. 13 shows the cross sectional view along plane 13—13 of FIG. 12. A square cross section prism 62 housed within the tubular housing 66 defines passageways 73 through which the liquid medium can flow.

The distal end of the prism can have various shapes. For example, as seen in FIG. 16, by utilizing a ball-tipped optical fiber 82 which has been beveled to the desired angle for total internal reflection, resulting prism 84 is less traumatic to tissue and the risk of breakage can be reduced.

Referring to FIG. 14, the distal tip of prism 62 (FIG. 11) can be frosted by means known in the art or coated with a layer of light absorbing material 80, such as charcoal or a ceramic, to convert the light energy to heat for ablation or coagulation of tissue in contact therewith.

The foregoing description and the drawings are intended as illustrative and are not to be taken as limiting. Still other variations and rearrangements of parts are possible and will readily present themselves to those skilled in the art.

We claim:

1. A catheter suitable for directing laser energy laterally to a selected site in a body lumen and comprising an elongated, hollow housing including a cap at the distal end of the catheter, defining a confined flow passageway for a liquid medium and a sidewall aperture in communication therewith through which said liquid medium flows;

a fiber optic, the distal end of which is mounted in said housing and the proximal end of which is adapted for coupling to a laser source; and a prism covered by said cap and, positioned in said liquid passageway to receive a laser beam emitted by the distal end of said fiber optic and to direct the emitted beam laterally relative to the longitudinal axis of the fiber optic;

said prism having a refractive index that is higher than the refractive index of said liquid medium in said liquid passageway contiguous with the reflective surface of the prism.

2. The catheter in accordance with claim 1 wherein the respective refractive index ratio for said prism and said liquid medium is at least 1.2.

3. The catheter in accordance with claim 1 wherein the distal end of said prism extends beyond said housing.

4. The catheter in accordance with claim 3 wherein the distal end of the prism is frosted or coated with a light energy absorbing substance.

5. The catheter in accordance with claim 1 wherein the refractive index of said prism is about 1.7 to about 2.6.

6. The catheter in accordance with claim 1 wherein said housing comprises an elongated apertured frame mounted to catheter tubing and defining said sidewall aperture, and wherein said prism is held by the frame in a spaced relationship to the fiber optic.

7. The catheter in accordance with claim 1 wherein the reflective surface of the prism has a substantially convex shape.

8. The catheter in accordance with claim 1 wherein the emissive surface of the prism has a substantially convex shape.

9. The catheter in accordance with claim 1 wherein the input surface of the prism has a convex shape having a curvature sufficient to collimate incoming energy from the fiber optic.

10. The catheter in accordance with claim 1 wherein the distal end of the prism fiber is formed into a ball shape, whose distal end has been beveled to an angle to achieve substantially total internal reflection.

11. The catheter in accordance with claim 1 wherein said housing includes an inner surface having ridges formed thereon and said prism includes an outer surface having depressions formed therein, said ridges matchingly engaging with said depressions to secure said prism within said housing.

12. A catheter suitable for directing laser energy laterally to a selected site in a body lumen and comprising:

an elongated, hollow cap at a distal end of the catheter, said cap including a sidewall aperture and defining a confined flow passageway for a liquid medium, said liquid medium flowing through said cap and out through said sidewall aperture;

a fiber optic including a distal end disposed in said cap and a proximal end for coupling to a laser source; and a prism positioned at the distal end of the catheter and covered by said cap, said prism being held in a spaced relationship from the fiber optic and positioned in said confined flow passageway to receive a laser beam emitted by said fiber optic and to direct the emitted beam outwardly through said sidewall aperture;

said prism having a refractive index that is higher than the refractive index of said liquid medium contiguous with the reflective surface of the prism.

13. The catheter in accordance with claim 12 wherein the respective refractive index ratio for said prism and said liquid medium is at least 1.2.

14. The catheter in accordance with claim 12 wherein refractive index of said prism is about 1.7 to 2.6.

15. The catheter in accordance with claim 12 wherein the reflective surface of the prism has a substantially convex shape.

16. The catheter in accordance with claim 12 wherein the emissive surface of the prism has a substantially convex shape.

17. The catheter in accordance with claim 12 wherein the input surface of the prism has a convex shape having a curvature sufficient to collimate incoming energy from the fiber optic.

18. The catheter in accordance with claim 12 wherein the distal end of the prism is formed into a ball shape, whose distal end has been beveled to an angle to achieve total internal reflection.

* * * * *